Figure 1:
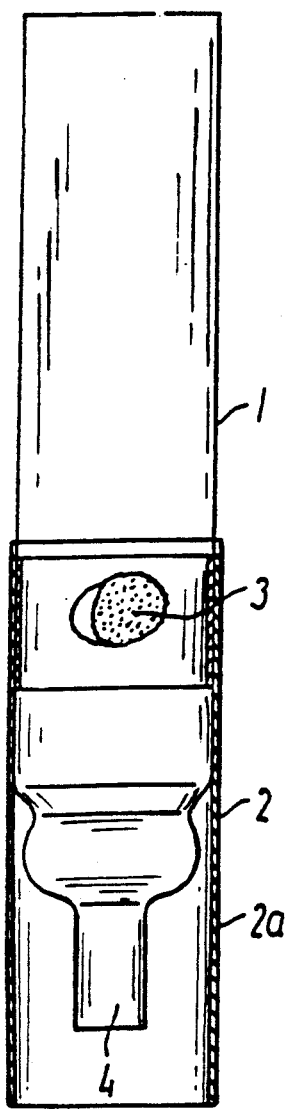

United States Patent [19]

Wendler

[11] Patent Number: 5,197,957
[45] Date of Patent: Mar. 30, 1993

[54] MALE URINE COLLECTION DEVICE

[75] Inventor: Henrik G. Wendler, Frederiksberg, Denmark

[73] Assignee: Coloplast A/S, Denmark

[21] Appl. No.: 901,756

[22] Filed: Jun. 22, 1992

[30] Foreign Application Priority Data

Jun. 21, 1991 [DK] Denmark .............................. 1217/91

[51] Int. Cl.⁵ ............................................. A61F 5/458
[52] U.S. Cl. ..................................... 604/352; 128/844
[58] Field of Search .............. 604/346, 347, 349, 351, 604/352, 353; 128/760, 844

[56] References Cited

U.S. PATENT DOCUMENTS

| | | | |
|---|---|---|---|
| Re. 33,206 | 5/1990 | Conway et al. ..................... | 604/349 |
| 2,389,831 | 11/1945 | Welsh .............................. | 604/352 X |
| 3,121,021 | 2/1964 | Copeland . | |
| 3,645,835 | 2/1972 | Hodgson ........................... | 602/54 X |
| 4,009,717 | 3/1977 | Allen ............................... | 604/347 |
| 4,626,250 | 12/1986 | Schneider ........................ | 604/353 X |
| 4,638,790 | 1/1987 | Conway et al. ................. | 604/352 X |
| 4,759,753 | 7/1988 | Schneider et al. ............... | 604/352 |
| 4,769,099 | 9/1988 | Therriault et al. ............. | 604/352 X |
| 4,846,909 | 7/1989 | Klug et al. . | |
| 4,863,449 | 9/1989 | Therriault et al. .............. | 604/352 |
| 4,885,049 | 12/1989 | Johannesson .................... | 604/349 X |
| 4,894,059 | 1/1990 | Larsen et al. ..................... | 604/349 |
| 4,934,382 | 6/1990 | Barone, Jr. ...................... | 604/349 X |
| 4,961,734 | 10/1990 | Kassman .......................... | 604/349 |
| 4,987,905 | 1/1991 | Broad, Jr. ........................ | 604/349 X |
| 5,059,190 | 10/1991 | Novak .............................. | 604/349 |
| 5,102,405 | 4/1992 | Conway et al. ................. | 604/352 |

FOREIGN PATENT DOCUMENTS

| | | | |
|---|---|---|---|
| 158131B | 10/1989 | Denmark . | |
| 0335564 | 10/1989 | European Pat. Off. ............ | 604/349 |
| 0358095 | 3/1990 | European Pat. Off. . | |
| 2649315 | 1/1991 | France .............................. | 128/844 |
| 8600816 | 2/1986 | PCT Int'l Appl. ................. | 604/349 |
| 8802624 | 4/1988 | PCT Int'l Appl. ................. | 604/349 |
| 9117728 | 11/1991 | PCT Int'l Appl. ................. | 604/349 |
| 2106784 | 4/1983 | United Kingdom ................ | 604/352 |
| 2172506 | 9/1986 | United Kingdom . | |
| 2198952 | 6/1988 | United Kingdom ................ | 604/349 |
| 2229922 | 10/1990 | United Kingdom ................ | 604/347 |

Primary Examiner—Randall L. Green
Assistant Examiner—Mary Beth O. Jones
Attorney, Agent, or Firm—Ostrolenk, Faber, Gerb & Soffen

[57] ABSTRACT

A device suitable for the collection of urine from a male, which device comprises a sheath (1) suitable for being fitted about a flaccid penis and comprising a thin flexible member of elastic material which is open at one end and is joined at the other end with a drainage tube portion (4) for connection with a collecting means. The sheath has an inner surface provided with a layer (3) of pressure sensitive adhesive and an outer surface and is rolled outwardly upon itself towards the drainage tube end (4) with successively larger turns, to form a torus (5). A separate thin flexible band (2) is interposed between successive turns of the rolled torus and has an adhesive rejecting surface facing the layer of pressure sensitive adhesive. A portion of the band (2a) extends outwardly from the turns of said rolled torus (5) so as to provide a free edge forming a gripping portion of the band and the band is in substantially non-adhering contact with the outer surface of the sheath, so that upon the sheath being unrolled onto a penis, the band (2) is removed from the sheath (1). The outwardly extending portion of the band (2a) preferably has the form of a skirt. The device avoids the numerous problems connected with silicone dipping, is easy to use and thanks to the gripping portion the adhesive is released from the release coated band without problems and the band is easily removed from the sheath.

14 Claims, 4 Drawing Sheets

MALE URINE COLLECTION DEVICE

The present invention relates to a male urine collection device, also known as a male external catheter or a self-sealing urisheath.

More specifically, the invention relates to a device suitable for the collection of urine from a male, which device comprises a sheath suitable for being fitted about a flaccid penis and comprising a thin flexible member of elastic material which is open at one end and is joined at the other end with a drainage tube portion for connection with a collecting means, said sheath having an inner surface of which at least an annular portion is provided with a layer of pressure sensitive adhesive and an outer surface and being rolled outwardly upon itself towards the drainage tube end with successively larger turns, to form a torus, and a separate thin flexible band interposed between successive turns of said rolled torus and having an adhesive rejecting surface facing the layer of pressure sensitive adhesive.

A device of this type is described in the assignee's application No. WO 86/00816 which has led inter alia to EP patent 187.846 and U.S. Pat. No. 4,885,049 and which are incorporated herein by reference. When it is unrolled onto a penis, it will be adhesively secured to the penis due to the adhesive on the inner surface.

A similar device is described in U.S. Pat. No. 4,863,449 where a thin flexible laminate is interposed between successive turns, said laminate comprising a first and second adhesive layer and an elastomeric layer therebetween. When the sheath is unrolled, the laminate will undergo delamination with the first adhesive layer remaining upon the sheath's inner surface for securing the sheath to the wearer and the second adhesive layer covered by the elastomeric layer, which acts as a release layer with regard to the first adhesive layer, remaining on the sheath's outer surface.

In U.S. Pat. No. 4,863,449 part of the pertinent prior art is discussed as follows.

U.S. Pat. NO. 4,626,250 depicts, in FIG. 18, a sheath for a male external catheter in which an adhesive coating 50 is disposed along the inner surface of the sheath's cylindrical body for adhesively securing the sheath to the penile shaft of a user. As indicated in FIG. 19, the sheath is supplied to the user in rolled form with the adhesive layer interposed between successive coils or turns and then, as the sheath is unrolled, the adhesive, which remains on the sheath's inner surface, is advanced into contact with the wearer. Effective application of the device obviously requires that the adhesive coating refrains from adhering to the sheath's outer surface as the sheath is unrolled and, as explained in the patent (column 10), any suitable release coating or interliner as well known in the tape industry and in other fields may be used for that purpose. In the example given, a silicone coating is provided on the sheath's outer surface to keep the adhesive 50 from adhering to that surface when the sheath is unrolled.

A common method for providing such a silicone coating during sheath manufacture is by a dipping step since other techniques, such as spraying, provide less control and create other problems in the workplace. Such problems are not entirely avoided even when a dipping process is used, since silicone tends to migrate even under carefully controlled working conditions, causing complications with equipment and silicone exposure to other surfaces not intended to be treated. Furthermore, the silicone baths into which catheter sheaths may be dipped tend to be very sensitive to ambient conditions. For example, under conditions of relatively high humidity, the useful life of such a bath may be greatly reduced, resulting in substantial material waste and increased manufacturing costs. Sheaths treated with silicone that has been adversely affected by humidity may be rendered unusable because the release coatings may not cure properly if at all. Furthermore, even after application and curing, silicone release coatings applied by dipping may prove troublesome, resulting in discoloration, blushing, flaking, cracking, and loss of release properties.

Some of these problems are summarized in International Patent Application PCT/DK85/00068, published Feb. 13, 1986 (corresponding to the abovementioned WO 86/00816 belonging to the present assignee). There, reference is made to the laborious prior art manufacturing procedures that first require forming of a catheter's body portion by immersing a mandrel into a latex solution, followed by rinsing and drying prior to the application of a silicone rubber layer, followed by curing of the silicone rubber layer before application of an adhesive which is then expected to transfer from the silicone rubber layer to the inside surface of the catheter when the product is rolled during the final stage of manufacture and later unrolled at time of use. Reference may also be had to U.S. Pat. No. 30 4,475,910 for discussion of the adhesive-transfer procedure.

Application PCT/DK85/00068 further discloses a procedure which eliminates the need for a silicone dipping step and thereby avoids many of the problems inherent in such a procedure. Unfortunately, the purported improvement is itself relatively complex, involving the application of an adhesive strip to one surface of the sheath and a silicone-bearing strip to the sheath's opposite surface. Means must be provided for inflating and deflating the sheath during processing in order to bring the strips into contact with the sheath's opposite surfaces at precise locations which will permit the adhesive and release coatings to register properly when the sheath is rolled in the final stage of manufacture.

A further disadvantage in connection with silicone dipping is that if the solvent for the silicone is not evaporated totally during the production, residues may be transferred to the bearer during the use.

Having experienced the drawbacks mentioned above, and especially a cold flow of the adhesives used for the application of the strips to the inner and outer surface of the sheath leading to severe ageing problems in that the sheaths could only be unrolled with great difficulty if at all, Applicant abandoned the described embodiment based on the use of strips. A production method was developed where the adhesive was sprayed onto a mandrel provided with a release surface of silicone rubber. A sheath of latex rubber was rolled onto the mandrel and subsequently dipped into a silicone bath, and after curing of the silicone the sheath was rolled off the mandrel. In a later developed improvement the sheath was mounted on an applicator as described in International Application WO 87/01582 corresponding to U.S. Pat. No. 4,894,059.

The described production method inter alia differs from the transfer method described in U.S. Pat. No. 4,475,910 and its Reissue patent No. 33.206 in that the adhesive is applied to the inner surface of the sheath and remains there at all times, while according to the method disclosed in the U.S. Pat. Nos. it is applied to the outer surface and transferred to the inner surface due to the unrolling.

For the sake of completeness, it should be mentioned that recently severe allergic reaction to latex devices has been reported, especially in cases of repeated exposure. In a number of cases adverse reactions have lead to death of the patients. It is believed that proteins in the latex itself is the primary source of the allergic reaction. Therefore, removal of as much of the water soluble proteins as possible from latex devices is recommended. This removal is primarily done by controlling the leaching process during production and immersing the devices in the leaching tanks for an appropriate time.

The in-line production method described in U.S. Pat. No. 4,475,910 and its Reissue patent does not lend itself to a thorough leaching of the latex sheaths. The same goes for the continuous method disclosed in EP application No. 471553.

During the development of the above mentioned production method Applicant not only experienced the problems described above with regard to silicone dipping, but also had severe problems with the curing and adherence of the silicone layer to the latex sheath.

It is well known that latex rubber contains various amounts of sulphur and nitrogen containing impurities, and also that latex rubber has a variating composition depending on its origin.

It turned out that the impurities in the latex inhibited the curing of the various silicones tested, so that either very long curing times were required or the silicone did not cure at all.

Also, in many cases the silicones did not release from the adhesive during unrolling.

To remedy this problem, Applicant developed a method where prior to the application of the silicone layer to the latex sheath a barrier layer was applied to the sheath, which was essentially impermeable to sulphur, sulphur compounds, nitrogen and nitrogen compounds released from the underlying latex sheath.

The method is described in more detail in DK patent application No. 2908/86 from which it appears that the preferred barrier layer was a polyurethane layer which was applied in liquid state based on a 1- or 2-component polyurethane material in an organic solvent.

This method was an undesirable compromise due to the necessity of an extra dipping bath and the environmental problems associated with the organic solvents and the highly toxic isocyanate components in the polyurethane.

The polyurethane dip was therefore abandoned when the Applicant finally found a silicone which had generally acceptable curing and release properties, following a direct application on the sheath.

Still, siliconized latex sheaths suffer from ageing problems and insufficient storage stability which manifest themselves as difficulties during unrolling. This may partly be due to impurities in the latex which may vary from one latex batch to another, and which alter the cured silicone and destroys its release properties vis a vis the adhesive during storage. Another frequent observation is that also in areas where there is no adhesive between the rolls, the latex somehow interferes with the silicone layer so that it adheres to the latex whereby the sheath can only be unrolled with great difficulty.

Of course, this problem can partly be taken care of during quality control by submitting samples of the rolled sheaths from each production to accelerated ageing test and reject those batches showing insufficient unrolling rather than releasing them to the customer. The rejection percentage varies over the year inter alia with the air humidity, temperature etc, but may be from about 5% up to about 30%, which is unacceptable from an economic point of view.

Obviously, this, together with the environmental and other problems described above in connection with silicone dipping, makes it highly desirable to provide a self-sealing urisheath which does not require a silicone dip during the manufacturing.

It is the object of the present invention to provide a solution to this problem.

Before describing in more detail the present solution to the problem of avoiding a silicone dip, the discussion of prior art external catheters will be elaborated although this prior art does not touch upon the silicone dip problems as such, but merely presents some more or less equivalent alternatives much along the lines of the earlier discussed U.S. Pat. No. 4,626,250 or simply refers to the need for a suitable release surface in order to permit unrolling.

Thus already based on the shortened discussion of U.S. Pat. No. 4,626,250 above an obvious substitution for the silicone release layer applied by dipping would be an interliner having a release coating. In fact, in cited column 10 it is directly stated that alternatively an interliner of the type also commonly used in the tape industry may be interposed between the adhesive coating and the outer surface of the sheath, such releasable interliner being stripped away by the user to expose the adhesive as the sheath is unrolled.

In the tape industry it is well known that when the adhesive is being stored in such a manner that the adhesive can come into contact with the backing material, e.g. if stored in the form of a reel, precautions must be taken to ensure that the adhesive does not strongly adhere to the backing material. For this purpose, the backing material may be provided with a release coating, e.g. a urethane copolymer, a silicone varnish or a methacrylate copolymer or else a release coated protector or interliner e.g. a silicone release coated paper or film may be applied over the adhesive surface.

For the sake of completeness, reference is made to U.S. Pat. No. 3,121,021 and 3,645,835 and Japanese patent publication No. 36-7539.

Also from U.S. Pat. No. 2,389,831 it is known to provide an adhesive layer on the inside of a prophylactic sheath for a body appendance with a strip of gauze, which is removed in order to expose the adhesive, before the sheath is completely unrolled. This necessity of a separate removal step has been regarded as cumbersome, and its avoidance was an important, feature in the grant of U.S. Pat. No. 4,475,910 and the corresponding UK patent No. 2.106.784.

Finally, US Pat. No. 4,846,909 describes a particular method of applying adhesive to the inside of a male external catheter. It is said that the inventive device will be packaged and sold in rolled condition which would create certain difficulties were it not for the presence of a non-stick layer.

Figure 3:
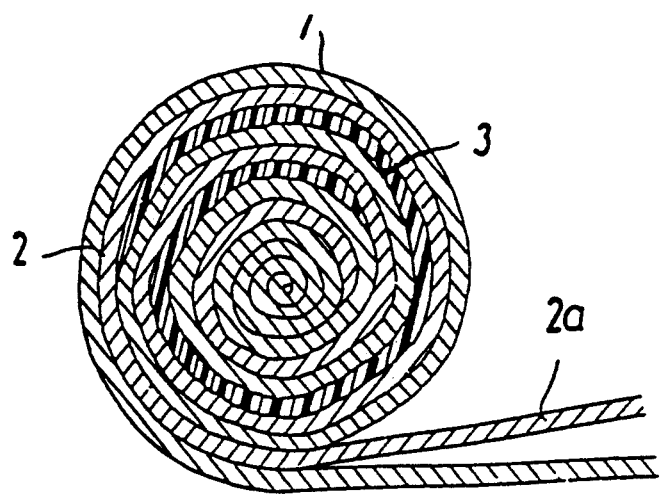

As shown in FIG. 3 of the patent, the sheath has provided along a portion of its length a coating of a non-stick non-adhesive substance which facilitates unrolling of the device along the penis. The layer is said to be e.g. a silicone rubber or other suitable elastomer or a teflon coating. However, the patent is silent as to how the layer is placed on the sheath, except that a pattern of release material is disposed on an external surface of the sheath before it is unrolled onto a mandrel provided with an adhesive pattern, and in a position such that upon unrolling of the sheath, the adhesive will communicate with the release material.

Turning now to the present invention, the solution to the silicone dip problem was found due to what might be regarded as an improvement of the abandoned strip concept described in the abovementioned WO 86/00816 according to which a cover foil strip having an adhesive rejecting surface was fastened to the outer surface of the body portion of the sheath by means of an adhesive layer. In its rolled condition the cover foil would be facing a pressure sensitive adhesive layer applied to the inner surface by means of the tape and be completely covered by the turns of what has been referred to above as the torus.

In relation to the present silicone dip problem, the application of a pressure sensitive adhesive layer to the inner surface of the sheath by means of a mandrel provided with an adhesive on top of a release surface of silicone rubber was not deemed to require any changes.

However, by applying a band provided with a release coating around the outer surface of the sheath while it was still positioned on the mandrel, said band being wider than the earlier proposed strip, so that a portion of the band extended outwardly from the turns of the torus formed by rolling the sheath off the mandrel, so that a free edge was provided, it proved possible not only to obtain a satisfactory release of the adhesive from the band during unrolling of the sheath, but also to remove the band from the sheath in a more simple manner than with common release liners or protective materials, e.g. according to U.S. Pat. No. 2,389,831.

This is due to the fact that the outwardly directed extension can serve as a gripping means.

Due to the extension of the band, it is also possible to avoid the adhesive contact between the band and the outside of the sheath which was deemed necessary for the earlier tape concept in order to prevent the tape from adhering to the adhesive on the inside rather than the sheath during the unrolling and thereby prevent the desired adhesive contact with the penis, provided that measures are taken during the unrolling to prevent the band from unrolling with the sheath, said measures simply being to grip the extension properly and maintain the grip until the sheath has been unrolled to such an extent that the upper edge of the band is laid free, whereupon the band can be removed simply by pulling.

The use of a separate band provided with a release coating has the further advantage that the release properties of a given batch of band material can be controlled before the individual bands are applied to the sheaths. This greatly reduces the rejection percentage mentioned above in connection with traditional silicone dips.

Also the fact that the band is removed from the sheath in connection with the unrolling secures that small amounts of adhesive which may not have released from the release coating are also removed.

The use of a separate band has the further advantage that it is not necessary to adapt the release coating to the individual sheath material, as was the case with the earlier silicone coatings. Still a further advantage is that the sheath is easier to unroll even after prolonged storage, since the interference between the silicone and the latex is avoided.

Consequently, the invention relates to a device suitable for the collection of urine from a male, which device comprises a sheath suitable for being fitted about a flaccid penis and comprising a thin flexible member of elastic material which is open at one end and is joined at the other end with a drainage tube portion for connection with a collecting means, said sheath having an inner surface provided with a layer of pressure sensitive adhesive and an outer surface and being rolled outwardly upon itself towards the drainage tube end with successively larger turns, to form a torus, and a separate thin flexible band interposed between successive turns of said rolled torus and having an adhesive rejecting surface facing the layer of pressure sensitive adhesive, and the device is characterized in that a portion of the band extends outwardly from the turns of said rolled torus so as to provide a free edge and that the band is in substantially non-adhering contact with the outer surface of the sheath, so that upon said sheath being unrolled onto a penis the band is removed from the sheath.

The outwardly extending portion of the band may have various forms as long as a sufficient area is provided to ensure that the band can be gripped and held firmly during the unrolling of the sheath onto the penis. It is crucial to a proper application of the device that the pressure sensitive adhesive is released from the band during the unrolling, or in other words that the band is not also unrolled, since this would prevent the sheath from adhering to the penis.

In one embodiment the outwardly extending portion has the form of a skirt. The length of the skirt may vary depending on the form of the sheath at the drainage end, often referred to as the neck portion. Thus, it is known to provide the end with a bulbous surge chamber between the neck portion and the drainage tube. Also constrictions may be formed on the neck portion to accomodate the rolled turns, e.g. as described in EP-390.720 Al (incorporated by reference). It is also known to provide accordion-like pleats at the end to obtain an anti-kink junction. The present invention is useful in connection with all these various modifications known per se, as long as the length of the skirt's outwardly extending portion is sufficient to ensure a good grip during unrolling.

If desired, the band may be provided with one or more earlike portions at the free end so as to highlight the proper gripping area to the user, but in most cases a skirt like portion is preferred since it reduces the risk of a faulty grip.

In another embodiment the band extends beyond the drainage tube end where it may be sealed to facilitate the grip and totally avoid the risk that the part of the free edge of the band is caught by the turns during unrolling.

If desired, the band may be further extended backwards towards the open end beyond the torus, where it is closed by means of an easily openable closure, e.g. a peel welding.

In this manner the band effectively forms an integrated packing arrangement for the device.

Urine collection devices of the self-sealing type are frequently marketed with the rolled up sheath mounted on an applicator so as to facilitate the proper positioning on such a device onto the penis.

The present invention is particularly useful in connection with devices comprising an applicator since the applicator might assist in providing a good grip on the extending portion of the flexible band during the unrolling.

A presently preferred applicator is described in International Application No. WO 87/01582 which has led to U.S. Pat. No. 4,894,059, which are incorporated herein by reference.

In order to ensure that the band is not unrolled, the band may be attached to the inside or the outside of the applicator e.g. by means of an adhesive.

However, this measure is not necessary if at least part of the outwardly extending portion of the band is located on the outside of the applicator, since it may then easily be gripped. If desired, part of the band may be located inside the applicator and optionally attached thereto. This may be desirable to avoid problems during unrolling if the band is formed by two halves.

In order to facilitate unrolling, it is advantageous to interpose a strip between the successive turns of the torus, preferably on top of the flexible band. The rolloff strip may be made from a non-elastic plastics material, e.g. a polyethylene, which may advantageously also be provided with a release layer, e.g. of silicone. The use of such an unrolling strip is known per se, but may be particularly advantageous in connection with the flexible band proposed according to the invention, since if it extends beyond the upper edge of the band it might provide a safeguard that sheath is unrolled to a sufficient degree before the band is removed.

This effect can be further amplified if the strip is attached to the band, particularly on a small extension of the band in the unrolling direction.

In a particular embodiment the band extends beyond the end of the applicator on which the sheath is mounted and is sealed to form an easily openable closure, e.g. by means of peel welding.

Figure 2:
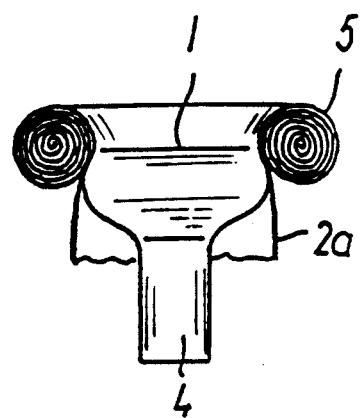
Figure 4:
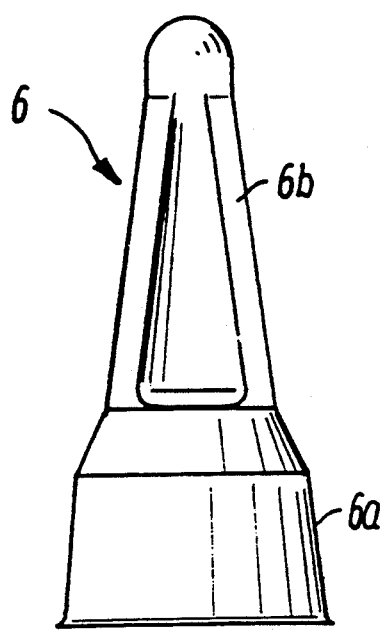
Figure 5:
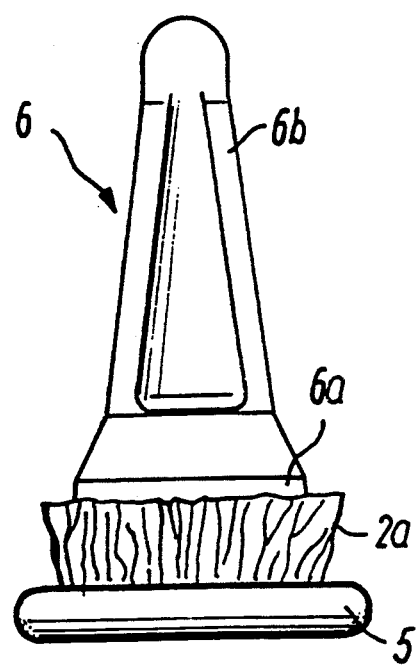
Figure 6:
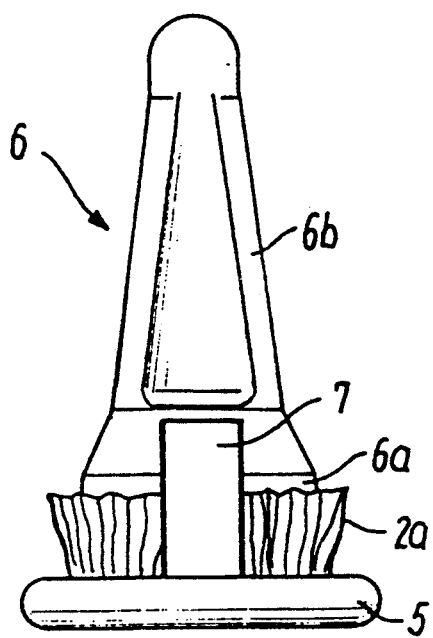
Figure 7:
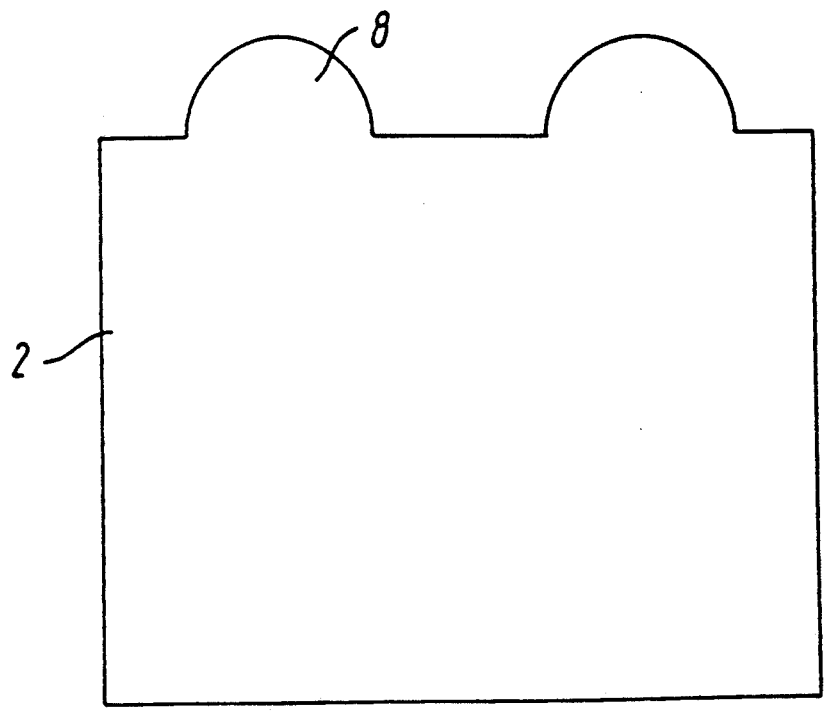
Figure 8:
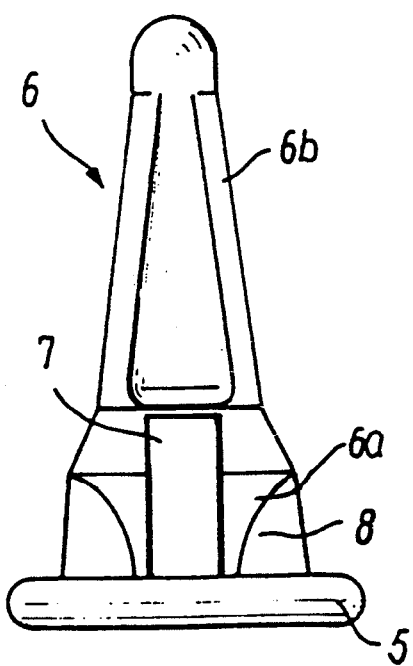

Embodiments of the invention will now be described by way of example, reference being made to the accompanying drawings, in which FIG. 1 is a longitudinal sectional view of an embodiment of a sheath forming part of the invention, FIG. 2 is a longitudinal sectional view of the sheath in its rolled-up supply condition, FIG. 3 is a detail of FIG. 2 on a larger scale, FIG. 4 is a schematic drawing of an applicator used in an embodiment of the invention, FIG. 5 shows an embodiment of the device in its supply condition, FIG. 6 shows a preferred embodiment provided with a strip to facilitate unrolling, FIG. 7 shows an embodiment of the band used in the device, FIG. 8 shows an embodiment of the device according to the invention incorporating a band according to FIG. 7 and an unrolling strip.

Figure 9:
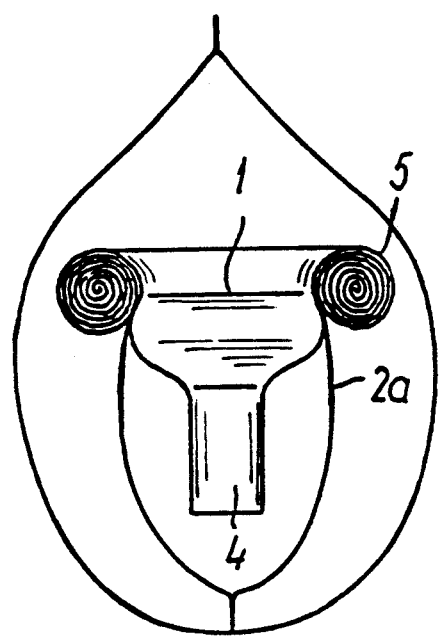

FIG. 9 is a longitudinal sectional view of the sheath in its rolled-up supplied condition with the band positioned to form an integrated packaging arrangement for the device.

In the embodiment of FIG. 1 the sheath comprises a substantially cylindrical body portion 1 having a diameter corresponding to a normal flaccid penis. The body portion 1 is manufactured as a soft, thin-walled single-layer component of an elastic material, e.g. latex or a synthetic rubber.

At one end the body portion 1 merges into a narrowed drainage tube portion 4 for connecting the catheter with a urine collecting bag not shown through a tube that is likewise not shown. Such collecting bag may in a manner known per se be adapted to be mounted for instance on one leg of the user.

At some distance from its drainage tube end, the body portion is provided on its inner surface with an adhesive layer 3 of a skin-friendly pressure sensitive adhesive, preferably by means of a mandrel not shown.

Opposite the adhesive at the outer surface an adhesive rejecting band 2 is provided which extends 2a beyond the narrowed portion, so that upon rolling the sheath outwardly upon itself to form a torus the band will extend outwardly from the torus to provide a free edge. The band can be made from commercially available release foils, comprising a thermoplastic elastomeric base layer provided with a release coating, but is preferably a polyurethane foil covered with a silicone release layer. If desired, the foil may be dyed, and/or provided with printings of various kinds. The band may be placed around the sheath, while it is still on the mandrel without the use of adhesive, since it was found that sufficient static electricity was generated to keep the band in place during the rolling off operation.

As shown in FIGS. 2 and 3 and 9 the device can be delivered in a rolled-up supply condition, thereby facilitating the arrangement. In the rolled-up condition the release surface of the band 2 faces the adhesive layer 3 so as to prevent successive turns of the torus 5 in the area of the adhesive layer from sticking to each other.

The adhesive layer may have any desired extension in the longitudinal direction of the sheath, but is preferably 3-4 cm.

If desired, more than one zone of adhesive layer may be applied provided that the band has a sufficient length to face all the zones, in the rolled-up condition.

It should be added that thanks to the use of the band in accordance with the present invention it is possible to move the adhesive closer to the drainage tube end, also known as the tip, than heretofore possible, if the sheath is mounted on an applicator as explained below. This may be an advantage in connection with small penises to secure adhesive contact.

FIG. 4 schematically shows an embodiment of an applicator 6 of the type discussed in detail in application WO 87/01582, which preferably has a sufficient length of the open annular portion 6a to surround the glans throughout its length and a grip portion 6b.

FIG. 5 schematically shows a presently preferred embodiment of the device according to the invention, where the sheath has been unrolled onto the annular portion 6a of an applicator 6 retaining the rolled-up portion in the supply condition. The band 2 extends outwardly from the torus 5 to form a skirt-like portion 2a located on the outside of the applicator, to which it may be attached, if desired.

A still preferred embodiment is shown in FIG. 6, where a strip 7 of an unelastic material, e.g. a release coated polyethylene is interposed between the rolls of the torus on top of the band 2 to facilitate unrolling.

FIG. 7 shows an embodiment of a band before being applied to the sheath.

The band is generally rectangular, but can be provided with ear-like portions 8 on the lower edge to facilitate gripping.

In FIG. 8 a device incorporating the band according to FIG. 7 is shown. In the figure only the ear-like portions 8 extend outwardly from the torus to form a free gripping edge.

Preferably, also a portion of the upper edge on which the ear-like portions are provided extend outwardly to reduce the risk of an unrolling of the band which would interfere with the adhesion to the penis.

FIG. 9 shows the device in the same rolled-up condition as shown in FIG. 2 in which the skirt-like portion 2a is sealed at the end of the drainage tube portion 4 and folded back so that it extends beyond the torus and is peel welded so as to form an integrated packing arrangement for the device.

The use of the device according to the invention will be further explained with regard to the presently preferred embodiment according to FIG. 6, it being understood that the unrolling of sheaths which are not mounted on an applicator is made in a similar manner.

The open end of the annular portion 6a of the applicator 6 with the rolled-up sheath is placed around the glans and a slight external pressure is applied on the skirt-like portion 2a and the annular portion 6a, so that the skirt-like portion 2a is held firmly against the applicator to prevent the band 2 from unrolling with the sheath. The sheath is then unrolled onto the penis by means of the strip 7. During the unrolling the band 2 also serves as a positioning aid for the applicator and provides an improved stability during unrolling, since it connects the applicator with the sheath. When the sheath is unrolled to such an extent that both the band 2 and the release strip 7 is completely unrolled, the band is removed from the sheath by pulling the applicator away from the penis. If necessary, the unrolling is continued.

While the invention has been explained above with particular reference to latex sheaths it is understood that because of the substantially non-adhering contact between the band and the sheath similar advantages are achieved by using sheaths of other materials, e.g. thermoplastic polymers, as inter alia described in copending application no. WO91/17728 which is incorporated herein by reference.

I claim:

1. A device suitable for the collection of urine from a male, which device comprises a sheath (1) suitable for being fitted about a flaccid penis and comprising a thin flexible member of elastic material which is open at one end and is joined at the other end with a drainage tube portion (4) for connection with a collecting means, said sheath having an inner surface of which at least an annular portion is provided with a layer (3) of pressure sensitive adhesive and an outer surface and being rolled outwardly upon itself towards the drainage tube end with successively larger turns, to form a torus (5), and a separate thin flexible band (2) interposed between successive turns of said rolled torus and having an adhesive rejecting surface facing the layer of pressure sensitive adhesive, c h a r a c t e r i z e d in that a portion (2a, 8) of the band (2) extends outwardly from the turns of said rolled torus so as to provide a free edge forming a gripping portion of the band and that the band is in substantially non-adhering contact with the outer surface of the sheath, so that upon the sheath being unrolled onto a penis, the band (2) is removed from the sheath (1).

2. A device according to claim 1, wherein the outwardly extending portion (2a) of the band (2) has the form of a skirt.

3. A device according to claim 1, wherein the outwardly extending portion of the band (2) is provided with one or more ear-like portions (8) at the free edge.

4. A device according to claim 1, wherein the band extends beyond the end of the drainage tube portion (4).

5. A device according to claim 4, wherein the band is sealed at the end of the drainage tube portion (4) and folded back so that it extends beyond the torus and is peel welded so as to form an integrated packing arrangement for the device.

6. A device according to claim 1, wherein the sheath (1) is mounted on an applicator (6) retaining the rolled-up portion in the supply condition.

7. A device according to claim 6, wherein the flexible band (2) is attached to the applicator (6).

8. A device according to claim 6, wherein at least part of the outwardly extending portion (2a, 8) of the flexible band (2) is located on the outside of the applicator (6).

9. A device according to claim 1, wherein a strip (7) is interposed between the successive turns of the torus (5) to facilitate unrolling.

10. A device according to claim 9, wherein the strip (7) is located on top of the flexible band (2).

11. A device according to claims 9, wherein the strip (7) is attached to the flexible band (2).

12. A device according to claim 6, wherein the band (2) extends beyond the end of the applicator (6) on which the sheath is mounted and is sealed so as to form an integrated packing arrangement for the device.

13. A device according to claim 1, wherein the flexible band (2) comprises a base layer of a plastics film provided with an adhesive rejecting outer layer.

14. A device according to claim 1, wherein the flexible band comprises a base layer of a polyurethane film provided with an adhesive rejecting silicone layer.

* * * * *